United States Patent
Kim et al.

(10) Patent No.: US 12,006,405 B2
(45) Date of Patent: Jun. 11, 2024

(54) SUPER ABSORBENT POLYMER AND METHOD FOR PRODUCING SAME

(71) Applicant: LG Chem, Ltd., Seoul (KR)

(72) Inventors: Kyu Pal Kim, Daejeon (KR); Gi Cheul Kim, Daejeon (KR); Sung Soo Park, Daejeon (KR)

(73) Assignee: LG Chem, Ltd., Seoul (KR)

( * ) Notice: Subject to any disclaimer, the term of this patent is extended or adjusted under 35 U.S.C. 154(b) by 153 days.

(21) Appl. No.: 15/774,496

(22) PCT Filed: Jun. 23, 2016

(86) PCT No.: PCT/KR2016/006697
§ 371 (c)(1),
(2) Date: May 8, 2018

(87) PCT Pub. No.: WO2017/209339
PCT Pub. Date: Dec. 7, 2017

(65) Prior Publication Data
US 2020/0123329 A1    Apr. 23, 2020

(30) Foreign Application Priority Data
Jun. 1, 2016 (KR) .................. 10-2016-0068375

(51) Int. Cl.
| | | |
|---|---|---|
| *C08J 3/075* | (2006.01) | |
| *C08F 20/04* | (2006.01) | |
| *C08J 3/12* | (2006.01) | |
| *C08J 3/24* | (2006.01) | |
| *C08K 3/34* | (2006.01) | |
| *C08K 5/053* | (2006.01) | |
| *C08K 5/11* | (2006.01) | |
| *C08K 5/1565* | (2006.01) | |

(52) U.S. Cl.
CPC .............. *C08J 3/075* (2013.01); *C08F 20/04* (2013.01); *C08J 3/12* (2013.01); *C08J 3/245* (2013.01); *C08K 3/34* (2013.01); *C08K 5/053* (2013.01); *C08K 5/11* (2013.01); *C08K 5/1565* (2013.01); *C08J 2300/14* (2013.01); *C08J 2333/08* (2013.01)

(58) Field of Classification Search
None
See application file for complete search history.

(56) References Cited

U.S. PATENT DOCUMENTS

| | | | | |
|---|---|---|---|---|
| 6,124,391 A | * | 9/2000 | Sun | A61L 15/18 523/223 |
| 7,329,701 B2 | * | 2/2008 | Herfert | A61F 13/534 524/445 |
| 9,950,308 B2 | * | 4/2018 | Lee | A61L 15/60 |
| 10,654,959 B2 | * | 5/2020 | Lee | C08F 220/06 |
| 2001/0055461 A1 | | 12/2001 | Tomaru et al. | |
| 2004/0180189 A1 | | 9/2004 | Funk et al. | |
| 2005/0245393 A1 | * | 11/2005 | Herfert | A61L 15/60 502/402 |
| 2010/0036004 A1 | | 2/2010 | Harren et al. | |
| 2010/0100066 A1 | | 4/2010 | Azad et al. | |
| 2010/0210746 A1 | | 8/2010 | Gustafson et al. | |
| 2010/0240808 A1 | | 9/2010 | Wada et al. | |
| 2012/0035294 A1 | * | 2/2012 | Kim | C08F 2/48 522/154 |
| 2012/0267570 A1 | | 10/2012 | Shi et al. | |
| 2015/0283284 A1 | | 10/2015 | Azad et al. | |
| 2016/0051966 A1 | | 2/2016 | Kotake et al. | |
| 2016/0207226 A1 | | 7/2016 | Torii et al. | |
| 2016/0375171 A1 | | 12/2016 | Omori et al. | |

FOREIGN PATENT DOCUMENTS

| | | | |
|---|---|---|---|
| EP | 0799861 A1 | 10/1997 | |
| EP | 2905071 A1 | 8/2015 | |
| EP | 3165542 A1 | 5/2017 | |
| JP | H1156143 A | 3/1999 | |
| JP | 3063903 U | 12/1999 | |
| JP | 2000236765 A | 9/2000 | |
| JP | 2004156010 A | 6/2004 | |
| JP | 2008527058 A | 7/2008 | |
| JP | 2009114391 A | 5/2009 | |
| KR | 20090108736 A | 10/2009 | |
| KR | 20100076980 A | 7/2010 | |
| KR | 20110086057 A | 7/2011 | |
| KR | 20150135325 A | 12/2015 | |
| KR | 20160048842 A | 5/2016 | |
| WO | WO-2004018006 A1 * | 3/2004 | ............. C08K 3/346 |
| WO | 2014094892 A1 | 6/2014 | |
| WO | WO-2015016643 A1 * | 2/2015 | ............. A61L 15/60 |

(Continued)

OTHER PUBLICATIONS

Extended European Search Report and Written Opinion for EP Application No. 16904138.1, dated Nov. 26, 2018.

(Continued)

*Primary Examiner* — Satya B Sastri
(74) *Attorney, Agent, or Firm* — Lerner David LLP

(57) ABSTRACT

The present invention relates to a super absorbent polymer and a method for producing same. The super absorbent polymer can achieve a high deodorizing function while exhibiting excellent absorption properties. As such, by using the super absorbent polymer, adult diapers having a thin thickness and high deodorizing function can be provided.

14 Claims, No Drawings

(56) References Cited

FOREIGN PATENT DOCUMENTS

| WO | 2015093594 A1 | 6/2015 |
|---|---|---|
| WO | 2016056866 A1 | 4/2016 |

OTHER PUBLICATIONS

Third Party Observation for Application No. PCT/KR2016/006697 dated Sep. 28, 2018.
International Search Report for Application No. PCT/KR2016/006697 dated Apr. 26, 2017.
Odian, George, "Principles of Polyermization." Second Edition, (Wiley, 1981), p. 203.
Schwalm, Reinhold, "UV Coatings: Basics, Recent Developments and New Applications." Elsevier Science, Dec. 21, 2006, p. 115.

* cited by examiner

SUPER ABSORBENT POLYMER AND METHOD FOR PRODUCING SAME

CROSS-REFERENCE TO RELATED APPLICATION(S)

The present application is a national phase entry under 35 U.S.C. § 371 of International Application No. PCT/KR2016/006697, filed Jun. 23, 2016, which claims priority from Korean Patent Application No. 10-2016-0068375, filed on Jun. 1, 2016, the disclosures of which are incorporated herein by reference in its entirety.

TECHNICAL FIELD

The present invention relates to a super absorbent polymer and a method for producing the same.

BACKGROUND ART

Super absorbent polymer (SAP) is a synthetic polymer material capable of absorbing moisture from about 500 to about 1,000 times its own weight, and each manufacturer has denominated it as different names such as SAM (Super Absorbency Material), AGM (Absorbent Gel Material) or the like. Such super absorbent polymers started to be practically applied in sanitary products, and now they are widely used for preparation of various products, for example, hygiene products such as paper diapers for children or sanitary napkins, water retaining soil products for gardening, water stop materials for the civil engineering and construction, sheets for raising seedling, fresh-keeping agents for food distribution fields, materials for poultice or the like. In most cases, these super absorbent polymers have been widely used in the field of hygienic materials such as diapers or sanitary napkin.

Recently, as the average life expectancy has been lengthened and the number of elderly people has increased, the prevalence of urinary incontinence has increased. Accordingly, it is expected that the super absorbent polymer will be widely used for adult diapers. Unlike baby diapers, it is important that adult diapers have their thickness and malodor removal capacity so that the wearing of diapers is not exposed to the outside.

However, in order to reduce the thickness of a diaper, it is necessary to reduce the proportion of the fiber material in the diaper and increase the proportion of the super absorbent polymer, and thus the super absorbent polymer is required to have high absorption performance and liquid permeability so that it can play a role of the existing fiber material. Furtherermore, in order to remove malodor, the super absorbent polymer must achieve a high deodorizing function as well as a high absorption performance. However, in the case of adjusting the structure or physical properties of the super absorbent polymer for achieving the deodorizing function, various absorption performances are deteriorated and thus super absorbent polymers satisfying all of these required physical properties have not yet been introduced.

Therefore, many studies are needed to develop super absorbent polymers capable of having a high deodorizing function and providing a diaper with a thin thickness.

DETAILED DESCRIPTION OF THE INVENTION

Technical Problem

It is one object of the present invention to provide a super absorbent polymer capable of achieving excellent absorption properties and high deodorizing function.

It is another object of the present invention to provide a method for producing the super absorbent polymer.

Technical Solution

According to an embodiment of the invention, there is provided a super absorbent polymer comprising: a base resin powder including a cross-linked polymer of a water-soluble ethylenically unsaturated monomer having at least partially neutralized acidic groups; a surface cross-linked layer that is further cross-linked from the cross-linked polymer and is formed on the base resin powder; and an inorganic material, wherein the super absorbent polymer has an ammonia removal efficiency of 60% or more, a centrifuge retention capacity (CRC) for a physiological saline solution of 26 to 40 g/g, and an absorbency under load (AUL) under 0.9 psi for a physiological saline solution of 17 to 25 g/g.

The super absorbent polymer may have a pH of 5.3 to 6.0. In order to provide the super absorbent polymer, the base polymer powder may include a cross-linked polymer of a water-soluble ethylenically unsaturated monomer having an acidic group that is neutralized to 55 to 65 mol % with respect to the total monomer.

The inorganic material may be, for example, montmorillonite, saponite, nontronite, laponite, beidelite, hectorite, sauconite, stevensite, vermiculite, volkonskoite, magadite, medmontite, kenyaite, kaolin mineral, serpentine mineral, mica mineral, chlorite mineral, sepolite, palygorskite, bauxite or a mixture thereof.

The super absorbent polymer may exhibit the following features: a centrifuge retention capacity (CRC) for a physiological saline solution of 30 to 40 g/g, and an absorbency under load (AUL) under 0.9 psi for a physiological saline solution of 20 to 25 g/g.

Meanwhile, according to one embodiment of the invention, there is provided a method for producing a super absorbent polymer, the method comprising the steps of: carrying out a cross-linking polymerization of a water-soluble ethylenically unsaturated monomer having at least partially neutralized acidic groups and a monomer mixture containing an internal cross-linking agent to form a hydrogel polymer; drying, pulverizing, and classifying the hydrogel polymer to form a base polymer powder; and further cross-linking the surface of the base polymer powder in the presence of a surface cross-linking agent to form a surface cross-linked layer, and comprising adding an inorganic material in at least one of the step of forming the hydrogel polymer, the step of forming the base polymer powder and the step of forming the surface cross-linked layer.

The water-soluble ethylenically unsaturated monomer may include at least one selected from the group consisting of anionic monomers of acrylic acid, maleic acid, maleic anhydride, fumaric acid, crotonic acid, itaconic acid, sorbic acid, vinylphosphonic acid, vinylsulfonic acid, allylsulfonic acid, 2-(meth)acryloylethanesulfonic acid, 2-(meth)acryloyloxyethanesulfonic acid, 2-(meth)acryloylpropanesulfonic acid or 2-(meth)acrylamido-2-methylpropanesulfonic acid, and their salts; non-ionic, hydrophilic group-containing monomers of (meth)acrylamide, N-substituted (meth)acrylamide, 2-hydroxyethyl(meth)acrylate, 2-hydroxypropyl (meth)acrylate, methoxypolyethylene glycol(meth)acrylate or polyethylene glycol(meth)acrylate; and amino group-containing unsaturated monomers of (N,N)-dimethylaminoethyl (meth)acrylate or (N,N)-dimethylaminopropyl (meth) acrylamide, and their quaternary product.

In particular, the method for producing the super absorbent polymer may provide a super absorbent polymer having a pH of 5.3 to 6.0.

In order to provide a super absorbent polymer having such a pH range, as the water-soluble ethylenically unsaturated monomer, a water-soluble ethylenically unsaturatedmonomer having an acidic group that is neutralized to 55 to 65 mol % with respect to the total monomer can be used.

Examples of the internal cross-linking agent include at least one selected from the group consisting of polyethylene glycol diacrylate (PEGDA), glycerine diacrylate, glycerin triacrylate, unmodified or ethoxylated trimethylolpropane triacrylate (TMPTA), hexanediol diacrylate, and triethylene glycol diacrylate.

In the method for producing a super absorbent polymer, an inorganic material may be added in the step of forming the hydrogel polymer and the step of forming the base polymer. Such inorganic material may be added in an amount of 0.01 to 1.0 part by weight with respect to 100 parts by weight of the base polymer powder.

As the surface cross-linking agent, at least one polyol selected from the group consisting of ethylene glycol, propylene glycol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol and glycerol; or at least one carbonate-based compound selected from the group consisting of ethylene carbonate and propylene carbonate can be used.

Such a surface cross-linking agent may be used in an amount of about 0.01 to 3% by weight with respect to the total weight of the base polymer powder.

The surface cross-linked layer may be formed at a temperature of 100 to 250° C.

Meanwhile, the method for producing the super absorbent polymer may include forming a surface cross-linked layer or adding an acid after forming the surface cross-linked layer in order to provide a super absorbent resin having a pH of 5.3 to 6.0.

Advantageous Effects

The super absorbent polymer according to one embodiment of the invention can achieve a high deodorizing function while exhibiting excellent absorption properties. Thus, by using the super absorbent polymer, an adult diaper having a thin thickness and a high deodorizing function can be provided.

DETAILED DESCRIPTION OF THE EMBODIMENTS

Hereinafter, a super absorbent polymer and a method for producing the same according to specific embodiments of the invention will be described.

According to one embodiment of the invention, there is provided a super absorbent polymer comprising: a base resin powder including a cross-linked polymer of a water-soluble eth lenically unsaturated monomer having at least partially neutralized acidic groups; a surface cross-linked layer that is further cross-linked from the cross-linked polymer and is formed on the base resin powder; and an inorganic material, wherein the super absorbent polymer has an ammonia removal efficiency of 60% or more, a centrifuge retention capacity (CRC) for a physiological saline solution of 26 to 40 g/g, and an absorbency under load (AUL) under 0.9 psi for a physiological saline solution of 17 to 2.5 g/g.

The super absorbent polymer can achieve a high deodorizing function while exhibiting excellent absorption properties. Specifically, the super absorbent polymer can exhibit excellent absorption properties and unproved deodorizing function as its pH is adjusted to 5.3 to 6.0. If the pH range is less than 5.3, various absorption properties are very poor, and if the pH range exceeds 6.0, deodorizing function cannot be expected. Therefore, it is expected that the above-mentioned super absorbent polymer is useful not only for babydiapers but also for adult diapers requiring a high deodorizing function.

Hereinafter, the structure, manufacturing method and the like of the super absorbent polymer according to one embodiment of the invention will be described in more detail.

The method for producing a super absorbent polymer may comprise the steps of: carrying out a cross-linking polymerization of a water-soluble ethylenically unsaturated monomer having at least partially neutralized acidic groups and a monomer mixture containing an internal cross-linking agent to form a hydrogel polymer; drying, pulverizing, and classifying the hydrogel polymer to form a base polymer powder; and further cross-linking the surface of the base polymer powder in the presence of a surface cross-linking agent to form a surface cross-linked layer, and comprising adding an inorganic material in at least one of the step of forming the hydrogel polymer, the step of forming the base polymer powder and the step of forming the surface cross-linked layer.

In the method for producing a super absorbent polymer, the water-soluble ethylenically unsaturated monomer may include at least one selected from the group consisting of anionic monomers of (meth)acrylic acid, maleic acid, maleic anhydride, fumaric acid, crotonic acid, itaconic acid, sorbic acid, vinylphosphonic acid, vinylsulfonic acid, allylsulfonic acid, 2-(meth)acryloylethanesulfonic acid, 2-(meth)acryloyloxyethanesulfonic acid, 2-(meth)acryloylpropanesulfonic acid or 2-(meth)acrylamido-2-methylpropanesulfonic acid, and their salts; non-ionic, hydrophilic group-containing monomers of (meth)acrylamide, N-substituted (meth)acrylamide, 2-hydroxyethyl(meth)acrylate, 2-hydroxypropyl (meth)acrylate, methoxypolyethylene glycol(meth)acrylate or polyethylene glycol (meth)acrylate; and amino group-containing unsaturated monomers of (N,N)-dimethylaminoethyl (meth)acrylate or (N,N)-dimethylaminopropyl (meth) acrylamide, and their quaternary product.

The water-soluble ethylenically unsaturated monomer is composed of a monomer having t partially neutralized acidic groups. Specifically, the water-soluble ethylenically unsaturated monomer may be composed of a monomer having an acidic group that is neutralized to 55 to 75 mol %, 55 to 70 mol %, 55 to 65 mol %, or 55 to 60 mol % with respect to the total monomer. In particular, the water-soluble ethylenically unsaturated monomer is composed of a monomer having an acidic group that is neutralized to 55 to 65 mol % or 55 to 60 mol % with respect to the total monomer, and the super absorbent polymer produced by the above production method satisfies the above-mentioned pH range and thus can achieve an improved deodorizing function. As an example, the super absorbent polymer produced by the production method within the above pH range can exhibit an ammonia removal efficiency of 60% or more, 70% or more, 80% or more, 90% or more, 95% or more or 97% or more.

In this specification, the ammonia removal efficiency is a numerical value indicating to what extent the super absorbent polymer removes ammonia in the surrounding environment, the ammonia removal efficiency of 0% means that the super absorbent polymer does not remove ammonia in the surrounding environment at all, and the ammonia removal efficiency of 100% means that the super absorbent polymer has completely removed ammonia in the surrounding environment.

Specifically, the ammonia removal efficiency can be calculated by putting a super absorbent polymer and a constant concentration of ammonia in a sealed vinyl pack and measuring the concentration of ammonia remaining after a certain period of time. For more specific methods, refer to the method described in Test Examples described later.

Examples of the monomer having neutralized acidic groups include a monomer (a salt of an anionic monomer) in which an acidic group included in the anionic monomer is neutralized. More specifically, as the water-soluble ethylenically unsaturated monomer, acrylic acid or a salt thereof may be used, and when acrylic acid is used, at least a part thereof may be neutralized and used. The use of such monomers makes it possible to produce a super absorbent polymer having more excellent physical properties. For example, when an alkali metal salt of acrylic acid is used as the water-soluble ethylenically unsaturated monomer having at least partially neutralized acidic groups, acrylic acid may be used by neutralizing it with a neutralizing agent such as sodium hydroxide (NaOH). At this time, the degree of neutralization of the acrylic acid can be adjusted in the content range (55 to 75 mol %, 55 to 70 mol %, 55 to 65 mol % or 55 to 60 mol %) of the monomer having neutralized acidic groups with respect to the total monomer. Within this range, a super absorbent polymer having excellent deodorizing function without fear of precipitation during neutralization can be provided.

In the monomer mixture containing the water-soluble ethylenically unsaturated monomer, the concentration the water-soluble ethylenically unsaturated monomer may be about 20% to about 60% by weight, or about 30% to about 50% by weight, with respect to the total amount of the monomer mixture including respective raw materials described below, and a solvent, which may be appropriately adjusted in consideration of polymerization time, the reaction conditions and the like. However, if the concentration of the monomer is excessively low, the yield of the super absorbent polymer can be lowered and thus economical problems may arise. On the other hand, if the concentration is excessively high, it may arise problems in the processes, for example, a part of the monomer may be precipitated, or the pulverization efficiency may be lowered during pulverization of the polymerized hydrogel polymer, etc., and the physical properties of the super absorbent polymer may be deteriorated.

The internal cross-linking agent is included in the monomer mixture in order to carry out a cross-linking polymerization of the water-soluble ethylenically unsaturated monomer having at least partially neutralized acidic groups. The internal cross-linking agent is composed of a compound containing two or more crosslinkable functional groups in the molecule. The internal cross-linking agent may include a carbon-carbon double bond in the crosslinkable functional group for smooth cross-linking polymerization reaction of the above-mentioned water-soluble ethylenically unsaturated monomer. More specific examples of these internal cross-linking agents include at least one selected from the group consisting of polyethylene glycol diacrylate (PEGDA), glycerine diacrylate, glycerin triacrylate, unmodified or ethoxylated trimethylolpropane triacrylate (TMPTA), hexanediol diacrylate, and triethylene glycol diacrylate.

The internal cross-linking agent can be contained at a concentration of about 0.01 to about 2% by weight with respect to the monomer mixture, thereby forming a cross-linked polymer exhibiting high absorption rate while having excellent water absorption capacity and absorbency under load.

Meanwhile, the monomer mixture may further include a polymerizatiron initiator that is generally used in the production of a super absorbent polymer.

Specifically, the polymerization initiator can be appropriately selected depending on the polymerization method. When a thermal polymerization method is carried out, a thermal polymerization initiator is used. When a photo-polymerization method is carried out, a photo-polymerization initiator is used. When a hybrid polymerization method (a method using both thermal and photo) is used, both a thermal polymerization initiator and a photo-polymerization initiator can be used. However, even in the case of the photo-polymerization method, a certain amount of heat is generated by light irradiation such as ultraviolet irradiation or the like, and a certain amount of heat is generated in accordance with the progress of the polymerization reaction, which is an exothermic reaction, and thus, a thermal polymerization initiator may be further included.

The photo-polymerization initiator that can be used is not particularly limited by its constitution as long as it is a compound capable of forming a radical by light such as ultraviolet rays.

The photo-polymerization initiator used herein may include, for example, at least one selected from the group consisting of benzoin ether, dialkyl acetophenone, hydroxyl alkylketone, phenyl glyoxylate, benzyl dimethyl ketal, acyl phosphine and α-aminoketone. Meanwhile, specific examples the acylphosphine include diphenyl(2,4,6-trimethylbenzoyl)phosphine oxide, phenylbis(2,4,6-trimethylbenzoyl)phosphine oxide, ethyl(2,4,6-trimethylbenzoyl)phenylphosphinate, and the like. More various photo-polymerization initiators are well disclosed in "UV Coatings: Basics, Recent Developments and New Application" written by Reinhold Schwalm, (Elsevier, 2007), p 115, the content of which is incorporated herein by reference.

The photo-polymerization initiator may be added in a concentration of about 0.0001 to 1.0% by weight with respect to the monomer composition. When the concentration of the photo-polymerization initiator is too low, the polymerization rate may become slow, and when the concentration of the photo-polymerization initiator is too high, the molecular weight of the super absorbent polymer may be small and the physical properties may become uneven.

Further, as the thermal polymerization initiator, at least one selected from the group consisting of persulfate-based initiator, azo-based initiator, hydrogen peroxide and ascorbic acid can be used. Specifically, examples of the persulfate-based initiators include sodium persulfate ($Na_2S_2O_8$), potassium persulfate ($K_2S_2O_8$), ammonium persulfate (($NH_4$)$_2$$S_2O_8$) and the like, and examples of the azo-based initiator include 2,2-azobis(2-amidinopropane)dihydrochloride, 2,2-azobis-(N,N-dimethylene)isobutyramidine dihydrochloride, 2-(carbamoylazo)isobutylonitril, 2,2-azobis[2-(2-imidazolin-2-yl)propane]dihydrochloride, 4,4-azobis-(4-cyanovaleric acid) and the like. More various thermal polymerization initiators are well disclosed in "Principle of Polymerization" written by Odian, (Wiley, 1981), p 203, the content of which is incorporated herein by reference.

The thermal polymerization initiator may be included at a concentration of about 0.001 to about 1.0% by weight with respect to the monomer mixture. If the concentration of such a thermal polymerization initiator is too low, additional thermal polymerization hardly occurs and the effect due to the addition of the thermal polymerization initiator may be insignificant. If the concentration of the thermal polymerization initiator is excessively high, the molecular weight of the super absorbent polymer may be small and the physical properties may become uneven.

In addition, the monomer mixture may further include additives such as a thickener, a plasticizer, a preservation stabilizer, an antioxidant, and the like, if necessary.

The raw materials such as the water-soluble ethylenically unsaturated monomers, polymerization initiators, internal cross-linking agents and additives described above may be prepared in a form dissolved in a solvent.

Any usable solvent can be used without being limited by its constitution as long as it can dissolve the above-mentioned components. Examples of the solvent may include at least one selected from the group consisting of water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, N,N-dimethylacetamide, and the like.

The solvent may be contained in the residual amount excluding the above-mentioned components with respect to the total content of the monomer mixture.

Meanwhile, the method for polymerizing such a monomer mixture to form a hydrogel polymer is not particularly limited by its constitution as long as it is a polymerization method commonly used in the art.

Specifically, the polymerization process may be largely classified into a thermal polymerization and a photo-polymerization depending on a polymerization energy source. Usually, in the case of the thermal polymerization, it may be carried out in a reactor like a kneader equipped with stirring spindles. At this time, the polymerization temperature of the monomer mixture can be adjusted to about 30 to 110° C. to a hydrogel polymer having an appropriate cross-linking structure. Means for achieving the polymerization temperature within the above-described range is not particularly limited, and the heating can be carried out by providing a heating medium or directly providing a heating source. The type of heat medium that can be used here includes a heated fluid such as steam, hot air, hot oil, etc., but it is not limited to thereto. Further, the temperature of the heating medium to be provided can be appropriately selected in consideration of the means of the heating medium, the temperature raising speed, and the temperature raising target temperature. Meanwhile, as a heat source to be provided directly, there may be mentioned a heating method using electricity or a heating method using gas, but is not limited to the above example.

Meanwhile, in the case of the photo-polymerization, it may be carried out in a reactor equipped with a movable conveyor belt. However, the above-described polymerization method is an example only, and the present invention is not limited thereto.

For example, when the thermal polymerization is carried out by providing hot air to a reactor like a kneader equipped with the agitating spindles, or heating the reactor, the hydrogel polymer discharged from the outlet of the reactor can be obtained. The hydrogel polymer thus obtained can be in the form of several centimeters or several millimeters depending on the type of agitating spindles equipped in the reactor. Specifically, the size of the obtained hydrogel polymer may vary depending on the concentration of the monomer mixture to be injected thereto, the injection speed, or the like.

Further, as described above, when the photo-polymerization is carried out in a reactor equipped with a movable conveyor belt, the obtained hydrogel polymer may be usually a sheet-like hydrogel polymer having a width of the belt. The thickness of the polymer sheet may vary depending on the concentration of the monomer mixture to be injected thereto and the injection speed, but usually, it is preferable to supply the monomer mixture so that a sheet-like polymer having a thickness of about 0.5 to about 10 cm can be obtained. If the monomer mixture is supplied to such an extent that the thickness of the sheet-like polymer is too thin, it is undesirable because the production efficiency is low, and if the thickness of the sheet-like polymer is more than 10 cm, the polymerization reaction cannot be uniformly carried out over the entire thickness.

The polymerization time of the monomer mixture can be appropriately adjusted depending on the polymerization method to be used. As a non-limiting example, the polymerization time of the monomer mixture can be adjusted to about 30 seconds to 60 minutes to form a hydrogel polymer having a suitable cross-linking structure.

The hydrogel polymer obtained by the above-mentioned method may have a water content of about 30 to about 80% by weight. Meanwhile, the "water content" as used herein means a weight occupied by moisture with respect to a total amount of the hydrogel polymer, which may be the value obtained by subtracting the weight of the dried polymer from the weight of the hydrogel polymer. Specifically, the water content can be defined as a value calculated by measuring the weight loss due to evaporation of moisture in the polymer in the drying process by raising the temperature of the polymer through infrared heating. At this time, the water content is measured under the drying conditions determined as follows: the drying temperature is increased from room temperature to about 180° C. and then the temperature is maintained at 180° C., and the total drying time is set to 40 minutes, including 5 minutes for the temperature rising step.

After the monomers are polymerized into cross-linked polymer, the base polymer powder can be obtained through steps such as drying, pulverization, classification, and the like, and through the steps such as pulverization and classification, the base polymer powder and the super absorbent polymer obtained therefrom are suitably produced and provided so as to have a particle diameter of about 150 to 850 μm. More specifically, at least about 95% by weight or more of the base polymer powder and the super absorbent polymer obtained therefrom has a particle diameter of about 150 μm to 850 μm and a fine powder having a particle diameter of less than about 150 μm can contained in an amount of less than about by weight.

As the particle diameter distribution of the base polymer powder and the super absorbent polymer is adjusted to the preferable range as described above, super absorbent polymer finally produced can exhibit excellent absorption properties.

Meanwhile, the method of drying, pulverization and classification will be described in more detail.

First, in the drying of the hydrogel polymer, a step of coarse pulverization may be further carried out before drying to improve the efficiency of the drying step, if necessary.

In this regard, a pulverizing machine used may include, but its configuration is not limited to, for example, any one selected from the group consisting of a vertical pulverizing device, a turbo cutter, a turbo grinder, a rotary cutter mill, a cutter mill, a disc mill, a shred crusher, a crusher, a chopper, and a disc cutter. However, it is not limited to the above-described examples.

In this case, the coarsely pulverizing step may be carried out so that the particle diameter of the hydrogel polymer becomes about 0.2 to about 15 mm.

Pulverizing the hydrogel polymer into a particle diameter of less than 0.2 mm is technically not easy due to its high water content, and mutual agglomeration may occur between the pulverized particles. Meanwhile, if the polymer is pulverized into a particle diameter of greater than 15 mm, the effect of increasing the efficiency in the subsequent drying step may be insignificant.

The hydrogel polymer coarsely pulverized as described above or the hydrogel polymer immediately after polymerization without the coarsely pulverizing step is subjected to a drying step. In this case, the drying temperature of the drying step may be about 50° C. to about 250° C.

When the drying temperature is less than 50° C., it is likely that the drying time becomes too long and the physical properties of the super absorbent polymer finally formed are deteriorated, and when the drying temperature is higher than 250° C., only the surface of the polymer is excessively dried, and thus it is likely that fine powder may be generated during the subsequent pulverizing step and the physical properties of the super absorbent polymer finally formed is deteriorated.

Meanwhile, the drying time may be about 20 minutes to about 15 hours, in consideration of the process efficiency and the like, but it is not limited thereto.

The drying method may also be selected and used without being limited by its constitution if it is a method generally used for drying the hydrogel polymer. Specifically, the drying step may be carried out by a method such as hot air supply, infrared irradiation, microwave irradiation or ultraviolet irradiation. The water content of the polymer after such a drying step may be about 0.1% to about 10% by weight.

Next, a step of pulverizing the dried polymer obtained through such a drying step is carried out.

The polymer powder obtained after the pulverizing step may have a particle diameter of about 150 μm to about 850 μm. Specific examples of a pulverizing device that can be used for pulverizing the polymer to have the above particle size may include a pin mill, a hammer mill, a screw mill, a roll mill, a disc mill, a jog mill or the like, but it is not limited thereto.

Also, in order to control the physical properties of the super absorbent polymer powder finally commercialized after the pulverization step, a separate step of classifying the polymer powder obtained after the pulverization depending on the particle diameter may be undergone. Preferably, a polymer having a particle diameter of about 150 to about 850 μm is classified and only the polymer powder having such a particle diameter can be subjected to the surface cross-linking reaction and finally commercialized. Since the particle diameter distribution of the base polymer powder obtained through such a process has already been described above, a further detailed description thereof will be omitted.

Meanwhile, after the step of forming the base polymer powder described above, the surface cross-linked layer can be formed by further cross-linking the surface of the base polymer powder in the presence of the surface cross-linking agent, and thereby the super absorbent resin can be produced.

The surface cross-linking r can be formed by using a surface cross-linking agent conventionally used in the production of a super absorbent polymer. As the surface cross-linking agent, those known in the technical field to which the present invention belongs can be used without particular limitation. More specific examples of the surface cross-linking agent include polyols such as ethylene glycol, propylene glycol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol and glycerol; or carbonate compounds such as ethylene carbonate and propylene carbonate. Such a surface cross-linking agent may be used in an amount of about 0.01 to 3% by weight with respect to the total weight of the base polymer powder.

Further, in the surface cross-linking step, in addition to the above-mentioned surface cross-linking agent, at least one inorganic material selected from the group consisting of silica, clay, alumina, silica-alumina composite, titania, zinc oxide and aluminum sulfate can be added to carry out the surface cross-linking reaction.

The inorganic material may be used in the form of powder or liquid, and in particular, it can be used as alumina powder, silica-alumina powder, titania powder, or nanosilica solution. In addition, the inorganic material may be used in an amount of about 0.05 to about 2% by weight with respect to the total weight of the base polymer powder.

Furthermore, in the surface cross-linking step, the surface cross-linking structure of the super absorbent polymer can be further optimized as the surface cross-linking proceeds by adding a multivalent metal cation in place of or in addition to the inorganic material. This is predicted because these metal cations can further reduce the cross-linking distance by forming a chelate with the carboxyl group (COOH) of the super absorbent polymer.

The method of adding the surface cross-linking agent and optionally an inorganic material and/or a polyvalent metal cation to the base polymer powder is not particularly limited by its construction. For example, a method of adding a surface cross-linking agent and a base polymer powder to a reaction tank and mixing them, a method of spraying a surface cross-linking agent or the like onto the base polymer powder, a method continuously providing a base polymer powder and a surface cross-linking agent to a continuously operated mixer, or the like, can be used.

When the surface cross-linking agent is added, water and/or methanol can be additionally mixed and added. When water and methanol are added, there is an advantage that the surface cross-linking agent can be uniformly dispersed in the base polymer powder. At this time, the content of water and methanol to be added can be appropriately adjusted for the purpose of inducing uniform dispersion of the surface cross-linking agent, preventing the aggregation phenomenon of the base polymer powder, and optimizing the penetration depth of the surface of the cross-linking agent.

The surface cross-linking reaction can be carried out by heating the base polymer powder to which the surface cross-linking agent is added at about 100° C. or more for about 20 minutes or longer. In particular, in order to produce a super absorbent polymer which can more effectively exhibit the above-mentioned effects, the conditions of the surface cross-linking step can be adjusted so that the maximum reaction temperature is about 100 to 250° C.

Then, the retention time at the maximum action temperature can be adjusted to conditions of about 20 minutes or more, or about 20 minutes to 2 hour or less. In addition, the temperature raising time required to reach from a temperature at the start of the first reaction, for example, a temperature of about 100° C. or more, to the maximum reaction temperature can be controlled to about 5 minutes or more, or about 5 minutes or more and 1 hour less.

The temperature raising means for the surface cross-linking reaction is not particularly limited. The temperature raising means used for polymerizing the monomer mixture can be used.

Meanwhile, the above production method comprises adding an inorganic material in at least one of the step of forming the hydrogel polymer, the step of forming the base polymer powder and the step of forming the surface cross-linked layer.

In the above production method, it s possible to provide a super absorbent polymer whose pH is adjusted to 5.3 to 6.0 in order to achieve improved deodorizing function.

As an example, in order to show the above-mentioned pH, as the water-soluble ethylenically unsaturated monomer, a monomer having an acidic group that is neutralized to 55 to 65 mol %, or 55 to 60 mol % with respect to the total monomer.

In the case of a monomer having an acidic group that is neutralized to more than 65 mol % or more than 65 mol % or more and 75 mol % or less with respect to the total monomer as a water-soluble ethylenically unsaturated monomer, there is a high possibility that it exceeds a pH of 6.0. Therefore, in such a case, in order to indicate the above-mentioned pH, an acid can be added after forming the surface cross-linked layer or after forming the surface cross-linked layer. Specific examples of these acids include citric acid, lactic acid, boric acid, boronic acid, ascorbic acid, acetic acid or a mixture thereof.

As described above, when the neutralization degree of the monomer is adjusted to a low level or an organic acid is added in order to exhibit the above-mentioned pH, the absorption properties of the super absorbent polymer may be deteriorated.

However, the present inventors have found that when an inorganic material is added during the production of a super absorbent polymer, it is possible to exhibit excellent absorption properties while realizing an improved deodorizing function.

The inorganic material may be, for example, montmorillonite, saponite, nontronite, laponite, beidelite, hectorite, sauconite, stevensite, vermiculite, volkonskoite, magadite, medmontite, kenyaite, kaolin mineral (including kaolinite, dickite and nacrite), serpentine mineral, mica mineral (including illite), chlorite mineral, sepolite, palygorskite, bauxite or a mixture thereof.

Among them, if laponite is used as the inorganic material, it is possible to exhibit excellent absorption properties along with an improved deodorizing function even when the pH of the super absorbent polymer is in the range of 5.3 to 6.0.

In the method for producing the super absorbent polymer, the method of adding the inorganic material is not particularly limited, and a predetermined amount of the inorganic material may be added once at any time, or continuously added for a certain period of time, or it may be added periodically twice or more.

The inorganic material may be added in the step of forming the hydrogel polymer and the step of forming the base resin powder. In such a case, it is possible to uniformly disperse the inorganic material in the hydrogel polymer, and to improve a bonding strength between the super absorbent polymer and the inorganic material.

The inorganic material may be added in an amount of 0.01 to 1.0 part by weight with respect to 100 parts by weight of the base resin powder. Within these ranges, excellent absorption properties and deodorizing functions can be realized at the same time.

The super absorbent polymer according to the above embodiment is produced by the above-mentioned production method and may comprise a base resin powder including a cross-linked polymer of a water-soluble ethylenically unsaturated monomer having at least partially neutralized acidic groups; a surface cross-linked layer that is further cross-linked from the cross-linked polymer and is formed on the base resin powder; and an inorganic material. The inorganic material may be distributed differently in the super absorbent polymer depending on the time of addition. As one example, when the inorganic material is added at least one time point of the steps of forming the hydrogel polymer and forming the base resin powder, the inorganic material is distributed evenly inside and outside the super absorbent polymer. When the inorganic material is added in the step of forming the surface cross-linking layer, it can be largely present on the surface of the super absorbent polymer.

The super absorbent polymer may have a centrifuge retention capacity (CRC) for a physiological saline solution of 26 to 40 g/g, 30 to 40 g/g, or 32 to 37 g/g, and an absorbency under load (AUL) under 0.9 psi for a physiological saline solution of 17 to 25 g/g, 20 to 25 g/g, or 21 to 23 g/g.

The centrifuge retention capacity (CRC) for a physiological saline solution can be measured according to EDANA recommended test method No. WSP 241.2. More specifically, the centrifuge retention capacity can be calculated according to the following Calculation Equation 1 after absorbing the super absorbent polymer in a physiological saline solution for 30 minutes:

$$CRC(g/g)=\{[W_2(g)-W_1(g)]/W_0(g)\}-1 \quad \text{[Calculation Equation 1]}$$

in the above calculation equation 1, $W_0$ (g) is an initial weight (g) of the super absorbent polymer, $W_1$ (g) is a weight of the empty bag not including the super absorbent polymer, which is measured after dehydrating the super absorbent polymer by using a centrifuge at 250 G for 3 minutes, and $W_2$ (g) is a weight of the bag including the super absorbent polymer, which is measured after immersing and absorbing the super absorbent polymer in a physiological saline solution (0.9 wt % sodium chloride aqueous solution) at room temperature for 30 minutes and then dehydrating the same by using a centrifuge at 250 G for 3 minutes.

Further, the absorbency under load (AUL) under 0.9 psi can be measured according to EDANA recommended test method No. WSP 242.2. More specifically, the absorbency under load can be calculated according to the following Calculation Equation 2 after absorbing the super absorbent polymer in a physiological saline solution under a load of about 0.9 psi for 1 hour:

$$AUP(g/g)=[W_4(g)-W_3(g)]/W_0(g) \quad \text{[Calculation Equation 2]}$$

in the above calculation equation 2, $W_0$ (g) is an initial weight (g) of the super absorbent polymer, $W_3$ (g) is the total sum of a weight of the super absorbent polymer and a weight of the device capable of providing a load to the super absorbent polymer, $W_4$ (g) is the total sum of a weight of the super absorbent polymer and a weight of the device capable of providing a load to the super absorbent polymer, after absorbing a physiological saline solution in the super absorbent polymer under a load (about 0.9 psi) for 1 hour.

$W_0$ (g) described in the above-mentioned calculation equations 1 and 2 corresponds to the initial weight (g) before absorbing the super absorbent polymer in a physiological saline solution and each may be the same or different.

Hereinafter, the action and effects of the present invention will be described in detail by way of specific Examples. However, these Examples are given for illustrative purposes only, and the scope of the invention is not intended to be limited thereto.

Example 1: Production of Super Absorbent Polymer

To the glass reactor were added 500 g of acrylic acid, 1.02 g polyethylene glycol diacrylate (weight average molecular weight ~500 g/mol) as an internal cross-linking agent, and 0.68 g of trimethylolpropane triacrylate containing 9 mol % of ethylene oxide (Ethoxylated-TMPTA, TMP (EO)9TA, M-3190 manufactured by Miwon Specialty Chemical Co., Ltd.). Then, 24 wt % caustic soda solution (NaOH aqueous solution) was slowly added dropwise so that about 60 mol % of acrylic acid could be neutralized with respect to the total amount of the acrylic acid. It was waited that, due to neutralization heat during dropwise addition of the caustic soda solution, the temperature of the monomer mixture was increased to about 72° C. or higher, and the monomer mixture was cooled.

When the temperature of the monomer mixture was cooled to about 45° C., the cooled monomer mixture was mixed with 28 g of the previously prepared sodium persulfate solution (diluted to 4% by weight in water), and the polymerization reaction was carried out while continuously adding the mixture through a supply opening of a polymerization reactor capable of kneading the mixture. At this time, the temperature of the polymerization reactor was maintained at 80° C., the maximum temperature of polymerization was 105° C., and the polymerization time was 1 minute and 15 seconds. Thereafter, the mixture was continuously kneaded to carry out polymerization and kneading for 20 minutes. The size of the hydrogel polymer thus produced was distributed to 0.2 cm or less. At this time, the water content of the finally formed hydrogel polymer was 51% by weight.

The hydrogel polymer obtained from the above polymerization reaction was passed through a hole having a diameter of 13 mm using a meat chopper to produce a crump.

Then, to the hydrogel polymer obtained above was added laponite so as to be present in about 0.5 part by weight per 100 parts by weight of the base resin powder. The crumps to which laponite was added were then dried in an oven capable of shifting airflow upward and downward. The crumps were uniformly dried by flowing hot air at 180° C. from the bottom to the top for 15 minutes and again from the top to the bottom for 15 minutes, and thereby a water content of the dried crump was set to 2% or less. The dried crump was pulverized using a pulverizing device and classified to obtain a base polymer powder having a size of 150 to 850 µm.

Thereafter, 100 g of the base polymer powder was mixed with a cross-linking agent solution obtained by mixing 3 g of water, 4.0 g of methanol and 0.15 g of ethylene carbonate, and then surface cross-linking reaction was carried out at 190° C. for 40 minutes. The resultant was pulverized and sieved to obtain a surface cross-linked super absorbent polymer having a particle diameter of 150 to 850 µm.

Example 2: Production of Super Absorbent Polymer

A surface cross-linked super absorbent polymer was produced in the same manner as in Example 1, except that 24 wt % caustic soda solution was slowly added dropwise so that about 55 mol % of acrylic acid could be neutralized with respect to the total acrylic acid in Example 1.

Example 3: Production of Super Absorbent Polymer

A surface cross-linked super absorbent polymer was produced in the same manner as in Example 1, except that 24 wt % caustic soda solution was slowly added dropwise so that about 73 mol % of acrylic acid was neutralized with respect to the total acrylic acid in Example 1. Then, 1.0 parts by weight of citric acid was added with respect to 100 parts by weight of the super absorbent polymer.

Comparative Example 1: Production of Super Absorbent Polymer

A surface cross-linked super absorbent polymer was produced in the same manner as in Example 1, except that a 24 wt % caustic soda solution was slowly added dropwise so that about 73 mol % of acrylic acid could be neutralized with respect to the total acrylic acid in Example 1, and laponite was not added.

Comparative Example 2: Production of Super Absorbent Polymer

A surface cross-linked super absorbent polymer was produced in the same manner as in Example 1, except that laponite was not added in Example 1.

Comparative Example 3: Production of Super Absorbent Polymer

A surface cross-linked super absorbent polymer was produced in the same manner as in Example 1, except that 24 wt % caustic soda solution was slowly added dropwise so that about 50 mol % of acrylic acid could be neutralized with respect to the total acrylic acid in Example 1.

Comparative Example 4: Production of Super Absorbent Polymer

A surface cross-linked super absorbent polymer was produced in the same manner as in Example 1, except that 24 wt % caustic soda solution was slowly added dropwise so that about 73 mol % of acrylic acid could be neutralized with respect to the total acrylic acid in Example 1.

Experimental Example: Evaluation of Physical Properties of Super Absorbent Polymer The physical properties of the super absorbent polymers prepared according to the above Examples and Comparative Examples were evaluated by the following methods, and the results are shown in Table 1 below.

(1) pH Measurement 100 g of a 0.9 wt % sodium chloride aqueous solution was added to a 200 mL beaker, and 0.5 g of surface cross-linked super absorbent polymer was added thereto and then stirred for 30 minutes. Thereafter, the pH of the solution was measured using a pH meter.

(2) Centrifuge Retention Capacity (CRC)

The centrifuge retention capacity (CRC) for a physiological saline solution was measured for the super absorbent polymers in accordance with EDANA recommended test method No. WSP 241.2.

Specifically, $W_0$ (g) (about 0.2 g) of the polymer was uniformly put in a nonwoven fabric-made bag, followed by sealing. Then, the bag was immersed in a physiological saline solution composed of 0.9 wt % aqueous sodium chloride solution (physiological saline solution) at room temperature. After 30 minutes, water was removed from the bag by centrifugation at 250 G for 3 minutes, and the weight $W_2$ (g) of the bag was then measured. Meanwhile, the same procedure was carried out using an empty bag not including the polymer, and then the resultant weight $W_1$ (g) was measured.

Using the respective weights thus obtained, centrifuge retention capacity was determined according to the following Calculation Equation 1.

$$CRC(g/g) = \{[W_2(g) - W_1(g)]/W_0(g)\} - 1 \quad \text{[Calculation Equation 1]}$$

in the above calculation equation 1, $W_0$ (g) is an initial weight (g) of the polymer, $W_1$ (g) is a weight of the empty bag not including the polymer, which is measured after dehydrating the polymer by using a centrifuge at 250 G for 3 minutes, and $W_2$ (g) is a weight of the bag including the polymer, which is measured after immersing and absorbing the polymer in a physiological saline solution at room temperature for 30 minutes and then dehydrating the same by using a centrifuge at 250 G for 3 minutes.

(3) Absorbency Under Load (AUL)

The absorbency under load (AUL) under 0.9 psi for a physiological saline solution was measured for the super absorbent polymers in accordance with EDANA recommended test method No. WSP 242.2.

Specifically, a 400 mesh stainless screen was installed in the bottom of a plastic cylinder having an inner diameter of 25 mm. $W_0$ (g)(about 0.16 g) of a super absorbent polymer for measuring the absorbency under load were uniformly scattered on the screen under the conditions of room temperature and relative humidity of 50%. Then, a piston which could provide a load of 6.3 kPa (0.9 psi) uniformly was put thereon. At this time, the piston used was designed so that the outer diameter was slightly smaller than 25 mm and thus it could move freely up and down without any gap with the inner wall of the cylinder. Then, the weight $W_3$ (g) of the device thus prepared was measured.

After putting a glass filter having a diameter of 90 mm and a thickness of 5 mm in a Petri dish having the diameter of 150 mm, 0.9 wt % sodium hydroxide aqueous solution (physiological saline solution) was poured in the Petri dish. At this time, the physiological saline solution was poured until the surface level became equal to the upper surface of the glass filter. Then, a sheet of filter paper having a diameter of 90 mm was put on the glass filter.

Subsequently, the prepared device was placed on the filter paper so that the super absorbent polymer in the device was swelled by a physiological saline solution under load. After one hour, the weight $W_4$ (g) of the device containing the swollen super absorbent polymer was measured.

Using the weight thus measured, the absorbency under load was calculated according to the following Calculation Equation 2.

$$AUL(g/g) = [W_4(g) - W_3(g)]/W_0(g) \quad \text{[Calculation Equation 2]}$$

in the above calculation equation 2, $W_0$ (g) is an initial weight (g) of the super absorbent polymer, $W_3$ is the total sum of a weight of the super absorbent polymer and a weight of the device capable of providing a load to the super absorbent polymer, $W_4$ (g) is the total sum of a weight of the super absorbent polymer and a weight of the device capable of providing a load to the super absorbent polymer, after absorbing a physiological saline solution in the super absorbent polymer under a load (about 0.9 psi) for 1 hour.

(4) Ammonia Removal Efficiency

Nitrogen was purged into a vinyl pack to prevent air from passing through, and then ammonia was injected at a concentration of 200 ppm ('A' in Calculation Equation 3 below). On the other hand, 2 g of surface cross-linked super absorbent polymer was added to another vinyl pack, purged with nitrogen, and sealed. Thereafter, ammonia gas prepared in advance was put in a vinyl pack containing the super absorbent polymer and left for 1 hour. Also, the concentration ('B' of Calculation Equation below) of the residual ammonia in the vinyl pack containing the super absorbent polymer was measured using a detection tube. Thereafter, the ammonia removal efficiency was calculated by the following Calculation Equation 3.

$$\text{Ammonia removal efficiency} = (A-B)/A*100 \quad \text{[Calculation Equation 3]}$$

TABLE 1

| | Inorganic material | Neutralization degree | pH | CRC [g/g] | AUP [g/g] | Ammonia removal efficiency [%] |
|---|---|---|---|---|---|---|
| Example 1 | Laponite | 60 mol % | 5.63 | 35.8 | 22.7 | 97 |
| Example 2 | Laponite | 55 mol % | 5.40 | 32.9 | 21.1 | 98 |
| Example 3 | Laponite | 73 mol % | 5.6 | 33.1 | 22.3 | 92 |
| Comparative Example 1 | Not added | 73 mol % | 6.1 | 33.5 | 23.5 | 40 |
| Comparative Example 2 | Not added | 60 mol % | 5.6 | 25.8 | 22.4 | 95 |
| Comparative Example 3 | Laponite | 50 mol % | 5.29 | 25.3 | 21.8 | 100 |
| Comparative Example 4 | Laponite | 73 mol % | 6.1 | 37.2 | 23.4 | 42 |

The invention claimed is:

1. A super absorbent polymer comprising: a base resin powder including a cross-linked polymer of a water-soluble ethylenically unsaturated monomer having at least partially neutralized acidic groups; a surface cross-linked layer that is further cross-linked from the cross-linked polymer and is formed on the base resin powder; and an inorganic material, wherein the super absorbent polymer has an ammonia removal efficiency of 92% to 98%, a centrifuge retention capacity (CRC) for a physiological saline solution of 32.9 to 35.8 g/g, and an absorbency under load (AUL) under 0.9 psi for a physiological saline solution of 21.1 to 23.4 g/g, wherein the inorganic material is laponite, wherein the superabsorbent polymer has a pH of 5.40 to 5.67, and wherein the inorganic material is present in an amount of 0.1 to 1.0 parts by weight with respect to 100 parts by weight of the base resin powder.

2. The super absorbent polymer of claim 1, wherein the cross-linked polymer is a cross-linked polymer of water-soluble ethylenically unsaturated monomer having an acidic group that is neutralized to 55 to 65 mol % with respect to the total monomer.

3. A method for producing the super absorbent polymer of claim 1, the method comprising the steps of: carrying out a cross-linking polymerization of a water-soluble ethylenically unsaturated monomer having at least partially neutralized acidic groups and a monomer mixture containing an internal cross-linking agent to form a hydrogel polymer; drying, pulverizing, and classifying the hydrogel polymer to form a base polymer powder; and further cross-linking the surface of the base polymer powder in the presence of a surface cross-linking agent to form a surface cross-linked layer, and comprising adding laponite as an inorganic material in at least one of the step of forming the hydrogel polymer, the step of forming the base polymer powder and the step of forming the surface cross-linked layer.

4. The method for producing the super absorbent polymer of claim 3, wherein the water-soluble ethylenically unsaturated monomer includes at least one of anionic monomers of (meth)acrylic acid, maleic acid, maleic anhydride, fumaric acid, crotonic acid, itaconic acid, sorbic acid, vinylphosphonic acid, vinylsulfonic acid, allylsulfonic acid, 2-(meth)acryloylethanesulfonic acid, 2-(meth)acryloyloxyethanesulfonic acid, 2-(meth)acryloylpropanesulfonic acid or 2-(meth)acrylamido-2-methylpropane sulfonic acid.

5. The method for producing the super absorbent polymer of claim 3, wherein it has a pH of 5.4 to 5.67.

6. The method for producing the super absorbent polymer of claim 3, using a water-soluble ethylenically unsaturated monomer having an acidic group that is neutralized to 55 to 65 mol % with respect to the total monomer can be used.

7. The method for producing the super absorbent polymer of claim 3, wherein the internal cross-linking agent includes at least one selected from the group consisting of polyethylene glycol diacrylate (PEGDA), glycerine diacrylate, glycerin triacrylate, unmodified or ethoxylated trimethylolpropane triacrylate (TMPTA), hexanediol diacrylate, and triethylene glycol diacrylate.

8. The method for producing the super absorbent polymer of claim 3, wherein an inorganic material is added in the step of forming the hydrogel polymer and the step of forming the base resin powder.

9. The method for producing the super absorbent polymer of claim 3, wherein the inorganic material is added in an amount of 0.1 to 1.0 part by weight with respect to 1.00 parts by weight of the base polymer powder.

10. The method for producing the super absorbent polymer of claim 3, wherein the surface cross-linking agent includes at least one polyol selected from the group consisting of ethylene glycol, propylene glycol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol and glycerol; or at least one carbonate-based compound selected from the group consisting of ethylene carbonate and propylene carbonate.

11. The method for producing the super absorbent polymer of claim 3, wherein the surface cross-linking agent is used in an amount of about 0.01 to 3% by weight with respect to the total weight of the base polymer powder.

12. The method for producing the super absorbent polymer of claim 3, wherein the surface cross-linked layer is formed at a temperature of 100 to 250° C.

13. The method for producing the super absorbent polymer of claim 3, comprising forming a surface cross-linked layer or adding an acid after forming the surface cross-linked layer.

14. The super absorbent polymer of claim 1, wherein the water-soluble ethylenically unsaturated monomer is acrylic acid.

* * * * *